(12) United States Patent
Meussen et al.

(10) Patent No.: US 6,691,822 B2
(45) Date of Patent: Feb. 17, 2004

(54) SOUND DAMPING FILTER, EAR PROTECTOR, AND METHOD FOR MANUFACTURING A MEMBRANE FOR A SOUND DAMPING

(75) Inventors: Victor Joseph Ahton Meussen, Krimpen a/d Lek (NL); Ronald Collee, Rotterdam (NL)

(73) Assignee: Groeneveld Elcea B.V., Dongen (NL)

( * ) Notice: Subject to any disclaimer, the term of this patent is extended or adjusted under 35 U.S.C. 154(b) by 0 days.

(21) Appl. No.: 10/200,732

(22) Filed: Jul. 22, 2002

(65) Prior Publication Data

US 2002/0179365 A1 Dec. 5, 2002

Related U.S. Application Data

(63) Continuation of application No. 09/561,555, filed on Apr. 28, 2000, now abandoned.

(51) Int. Cl.[7] .................................................. A61B 7/02
(52) U.S. Cl. ........................ 181/135; 181/129; 181/130
(58) Field of Search ................................ 181/129, 130, 181/135; 381/372, 382; 128/864, 865, 866, 867, 868; 2/209

(56) References Cited

U.S. PATENT DOCUMENTS 3,730,181 A * 5/1973 Fling ........................... 128/868
6,068,079 A * 5/2000 Hamery et al. ............. 181/135

* cited by examiner

*Primary Examiner*—Khanh Dang
(74) *Attorney, Agent, or Firm*—Kinney & Lange, P.A.

(57) ABSTRACT

A sound damping filter for an ear protector placeable in the auditory duct of a person. The sound damping filter comprises a sound damping canal with a passage extending from a sound inlet opening to a sound outlet opening. The passage of the sound damping canal is closed off by means of an air-permeable, sheetlike membrane, such that transport of air through the filter is possible. The invention also relates to an ear protector and a method for manufacturing a membrane for a sound damping filter.

24 Claims, 2 Drawing Sheets

SOUND DAMPING FILTER, EAR PROTECTOR, AND METHOD FOR MANUFACTURING A MEMBRANE FOR A SOUND DAMPING

CROSS REFERENCE TO RELATED APPLICATIONS

The present application is a continuation of U.S. patent application Ser. No. 09/561,555 filed on Apr. 28, 2000, abandoned.

BACKGROUND OF THE INVENTION

This invention relates to a sound damping filter for an ear protector placeable in the auditory duct of a person, comprising a sound damping canal with a passage extending from a sound inlet opening to a sound outlet opening.

Such a filter is known from practice and is utilized in a housing placeable in the auditory duct of a person in order to damp the intensity of sound to be supplied to the eardrum of the person. By varying the cross section and the length of the sound damping canal, the level of damping can be influenced, and a sound damping filter can be manufactured which is tailored to a particular application.

A disadvantage of the known filter is that the damping action of the damping canal is always stronger for higher sound frequencies than for lower frequencies. Consequently, the known filter has a damping characteristic rising, for instance, from 20 dB at 125 Hz to 40 dB at 8,000 Hz. A person wearing ear protectors in his ears which are tuned to damping machine noise of a frequency of about 50–500 Hz will perceive sound of a higher frequency, for instance the higher speech frequencies between 1 kHz and 3 kHz, only relatively weakly. Not only does this create the impression for the person that he is closed off from the environment, but also dangerous situations may arise in that the person perceives higher frequencies, for instance warning signals, unduly damped.

Also known are filters for ear protectors where the passage of the damping canal is closed off by means of a membrane, such that, during wearing, between the membrane and the eardrum of the person an amount of air is locked. Although an ear protector with such a filter enables a damping level that remains substantially the same over the audiofrequency range, there are disadvantages associated with this type of ear protector as well. In particular, the locked air volume has as a consequence that a wearer, due to conduction of the bones around the ear, has an enhanced perception of swallowing and chewing sounds, due to the so-called occlusion effect. In addition, the closure may give rise to transpiration in the auditory duct.

BRIEF SUMMARY OF THE INVENTION

The object of the invention is to provide a sound damping filter of the type mentioned in the opening paragraph hereof which does not possess the above-mentioned disadvantages. To that end, a sound damping filter according to the invention comprises a sound damping canal, the passage of which is closed off by means of an air permeable, sheetlike membrane, such that transport of air through the filter is possible. What is thus achieved is that a filter can be composed having a flatter damping characteristic, while through transport of air the occurrence of the occlusion effect and transpiration can be avoided.

The damping canal can then be chosen to have so large a diameter and/or so short a length that an increase of the damping of high frequencies is relatively small, whilst the membrane takes care of sufficient damping of low frequencies.

By adjustment of the geometry of the damping canal, the damping of high frequencies can be adjusted, without the damping for the low frequencies thereby being materially influenced. By adjustment of the geometry of the membrane and of the air permeability of the membrane, the damping of low frequencies can be set, without the damping for the high frequencies thereby being materially influenced.

Although the air permeability of the membrane can already be realized by the use of an air-permeable porous material which is provided with micropores, it is presently preferred to manufacture the membrane of substantially airtight material in which at least one perforation is provided. By increasing the number of perforations and/or the diameter thereof, the damping of low frequencies by the membrane can be reduced. By providing perforations of substantially equal diameter, the low tone damping can simply and reproducibly be stepwise influenced. What is achieved by choosing the diameter of the perforations to be substantially equal to the thickness of the membrane, is that low tone damping in practice can be set in a simple manner. What is achieved by the use of a flexible membrane is that in particular for higher frequencies a lower damping can be realized.

It is noted that when in this context reference is made to low frequencies, these are understood to include in any case frequencies lower than 1,000 Hz, while higher frequencies are understood to comprise at least frequencies higher than 1,000 Hz.

It is additionally noted that in this context a sheetlike membrane is understood to mean at least a membrane with a nonwoven structure.

Further advantageous embodiments of the invention are described in the dependent claims.

The invention further relates to an ear protector and to a method for manufacturing a membrane for a filter for an ear protector.

The invention will now be further elucidated on the basis of an exemplary embodiment represented in a drawing. In the drawing:

DETAILED DESCRIPTION OF THE INVENTION

Figure 2:
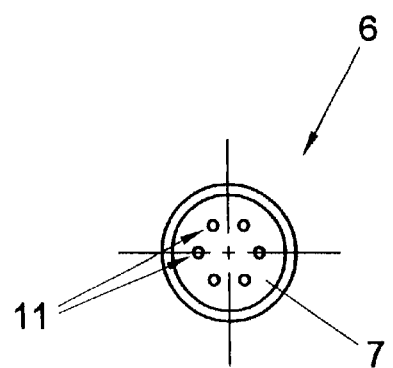
FIG. 2 shows a top plan view of the sound damping filter of FIG. 1 taken along the line II—II.

It is noted that the figures are only schematic representations of preferred embodiments of the invention. In the figures, the same or like parts have been indicated by corresponding reference numerals.

Figure 1:
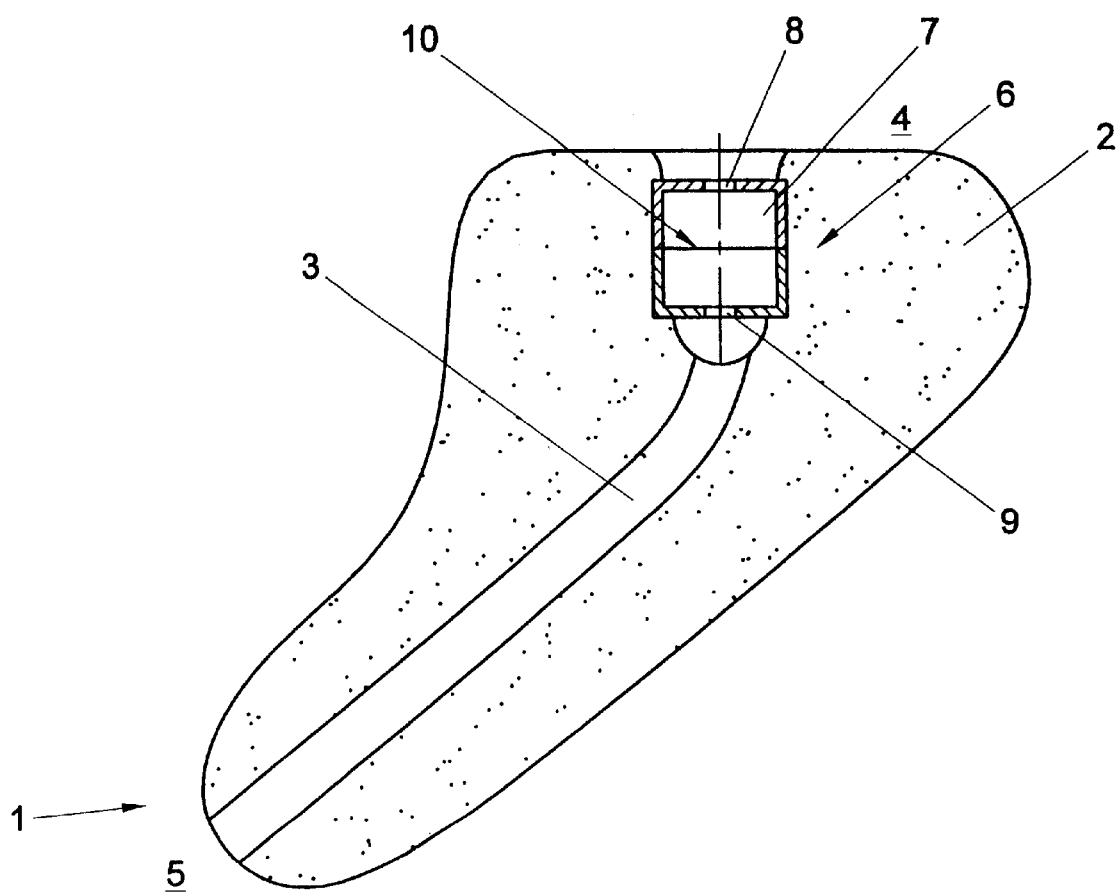
FIG. 1 shows a sectional side elevation of an ear protector with a sound damping filter according to the invention.

FIG. 1 shows an ear protector 1 having a housing 2 placeable in the auditory duct of a person. Such a housing 2 substantially closing off the auditory duct is generally known and is often designated by those skilled in the art by the name of otoplast. The housing 2 comprises a canal 3 which extends from a side 4 of the housing 2 which in use is located on the ear shell side of the ear, to the side 5 of the auditory duct which in use is located on the eardrum side of the ear. Fitted in the canal 3 is a sound damping filter 6 which is represented in top plan view in FIG. 2. The sound damping filter 6 comprises a sound damping canal 7 with a passage extending from a sound inlet opening 8 to a sound outlet opening 9.

The passage of the sound damping canal 7 is closed off by means of an air-permeable, sheetlike membrane 10. The membrane 10 has a thickness of about 30 $\mu$m in a direction transverse to the surface, and is manufactured of substantially airtight, sheetlike, flexible, plastic material. The material is preferably elastic. A suitable material is, for instance, LSR or another silicone material. The thickness of the membrane is preferably less than 0.1 mm and lies advantageously in the range of about 10 $\mu$m to about 50 $\mu$m. Provided in the membrane 10 are a number of perforations 11 which extend substantially transversely to the membrane surface, preferably perforations of a diameter of about 0.1 mm. For clarification, the perforations are represented on an enlarged scale in FIG. 2.

The membrane 10 can be fitted in the sound damping filter 6 by, for instance, building up the sound damping canal 7 in two parts and glueing the membrane between them. It will be clear to those skilled in the art that there are numerous other possibilities for providing the membrane in the sound damping canal. The membrane 10 can be fitted both tautly and slackly in the damping canal 7.

The extent of damping of sound waves of a low frequency can be influenced by varying the diameter and the number of the perforations 11, with a larger number of perforations and/or a greater diameter of the perforations leading to reduced-damping. In addition, the extent of damping can be influenced by adjusting the stiffness of the membrane, with a stiffer membrane leading to increased damping. The damping of sound waves of a high frequency can be influenced, inter alia, by adjusting, inter alia, the length and the diameter of the sound damping canal 7, the thickness of the membrane 10 and optionally the geometry of the canal 3.

Figure 3:
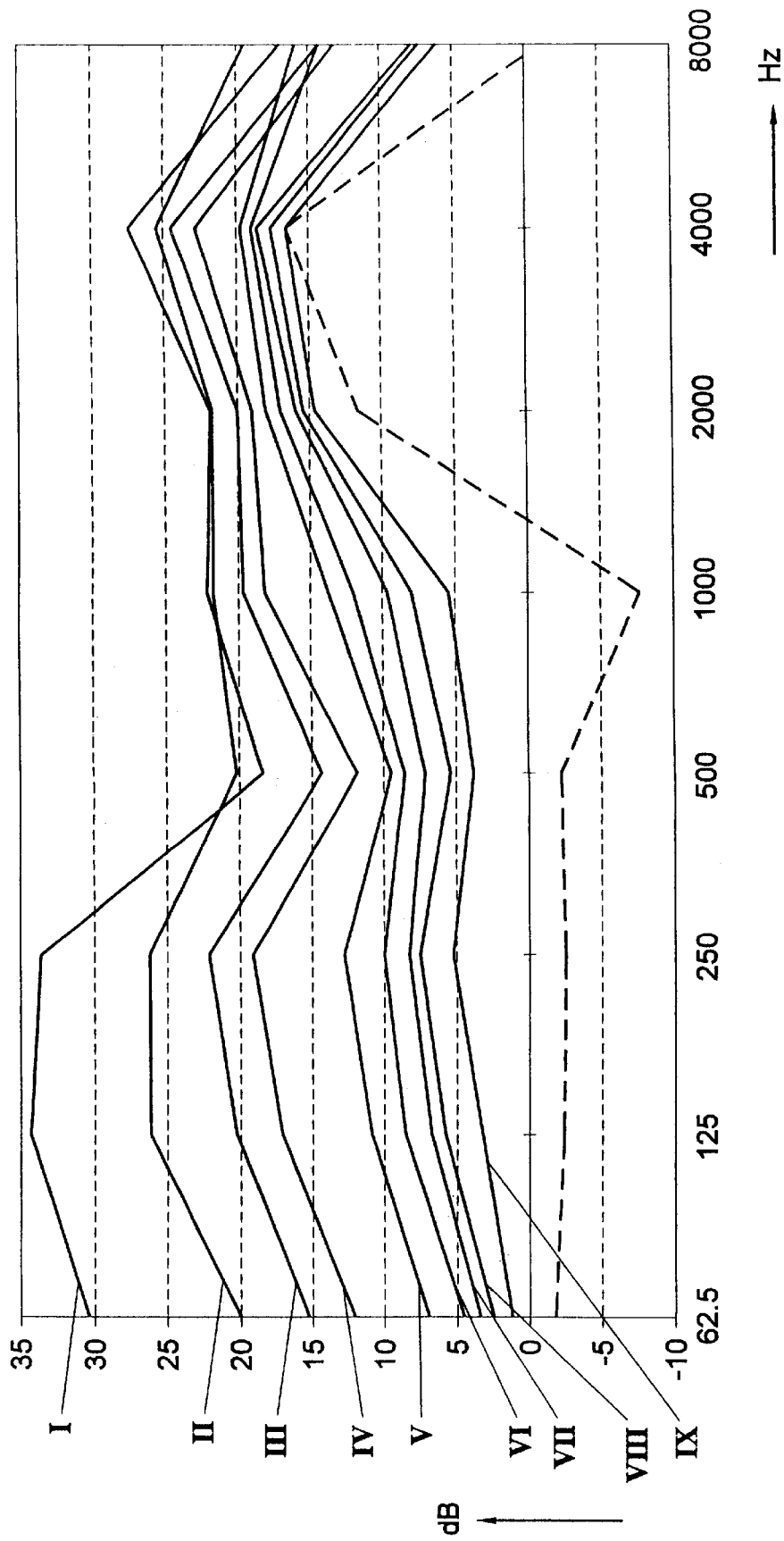
FIG. 3 shows a graph in which the damping is represented as a function of the frequency.

Referring to FIG. 3, the dash line therein represents the damping characteristic of the housing 2 without filter 6 in the canal 3. This damping characteristic depends inter alia on the shape of the auditory duct of the wearer and the selected geometry of the canal 3.

In FIG. 3, the line designated by reference numeral I reflects the damping as a function of the frequency for a filter having a membrane of a diameter of 4 mm and a thickness of 30 $\mu$m. By providing a single perforation 11 in the membrane, having a diameter of 0.1 mm, the damping characteristic designated by reference numeral II is achieved. By variation of the number of perforations 11 in the membrane 10, the low-frequency characteristic can be influenced as represented in the figure. The graphs respectively designated by reference numerals III, IV, V, VI, VII, VII, VIII and IX show the behavior for, respectively, four, eight, sixteen, twenty-four, thirty-two, forty and sixty-four perforations 11 of equal diameter.

In this way, starting from the too strong damping characteristic of the closed membrane as indicated by reference numeral I, the damping behavior for low frequencies can be adjusted by providing perforations 11 in the membrane 10. Advantageously, for instance four perforations can be provided, each having a diameter of about 0.1 mm, to obtain in the frequency range up to about 1,000 Hz a substantially flat damping characteristic or a damping characteristic otherwise adjusted to the conditions of use. As appears from FIG. 3, the damping decreases with increasing permeability of the membrane surface. Preferably, therefore, at most 5% of the membrane surface is air-permeable.

By adjustment of the position of the membrane in the sound damping canal 7 or the canal 3, optionally combined with the adjustment of the geometry of the canal 3, it is also possible to realize for the higher part of the frequency range a substantially flat damping characteristic or, if desired, a damping characteristic of a different configuration. Such adjustments to the geometry so as to influence the damping behavior at higher frequencies are known per se.

Advantageously, for instance a canal 3 can be manufactured having a substantially flat damping characteristic for higher frequencies. Thereupon, the damping characteristic for lower frequencies can be adjusted by providing the membrane 10, for instance through laser processing, with perforations 11 until the desired damping characteristic for lower frequencies has been achieved. What can be accomplished by providing perforations 11 of substantially equal diameter is that the adjustment of the damping characteristic for low frequencies can be carried out not only reproducibly, but also relatively simply. It is noted that it is also possible to provide perforations 11 in the membrane 10 prior to placement in the canal 7 of the filter 6 or the canal 3 of the housing 2. To shorten the time required for manufacture, the perforations 11 may optionally be provided simultaneously.

The invention is not limited to the preferred embodiments discussed here, but may also be practiced in other ways.

Thus, the membrane may also be fitted directly in the canal 3. In such a case, the sound damping canal 7 and the canal 3 coincide. Also, the sound damping filter may be used in combination with a confection earplug, that is, an ear protector which is not adapted to the auditory duct of a specific person. Further, it is possible that more sound damping canals 7 are present, which may or may not be provided with a membrane 10. Furthermore, the sound inlet opening 8 and/or the sound outlet opening 9 of the sound damping filter 6 can have the same diameter as the sound damping canal 7, and the sound damping canal 7 can include one or more bends and/or have a passage varying in size and/or shape. Also, two or more membranes 10 can be fitted in the damping canal 7, and the membrane may be provided with stiffening ribs or weakening grooves. In addition, the position of the membrane may vary in the longitudinal direction of the damping canal.

It is noted, further, that with increasing diameter of a perforation, damping decreases more strongly than linearly. Although it is possible, in order to achieve a desired damping, to provide one perforation of a relatively large diameter, it may be preferable from the viewpoint of manufacturing technique to provide a larger number of smaller perforations.

It is also noted that the diameter of the perforation(s) is preferably substantially equal to the thickness of the membrane. In particular, the diameter of the perforation(s) is preferably about 0.5 to 2× the thickness of the membrane, more preferably the diameter of the perforation(s) is 0.8 to 1.2× the thickness of the membrane.

Such variations will be clear to those skilled in the art and are understood to fall within the framework of the appended claims.

What is claimed is:

1. An ear protector for damping sound, the ear protector comprising:

a ear protector housing sized to fit in an auditory duct of a person, the ear protector housing having an ear shell side and an ear drum side, the ear protector housing substantially closing off the auditory duct of the person, the ear protector housing comprising;
  a canal extending from the ear shell side of the ear protector housing to the ear drum side; and
  a sound damping filter positioned within the canal, the sound damping filter comprising:
    a filter housing formed from a first material, the filter housing having a sound damping canal defining a passage extending from a sound inlet opening to a sound outlet opening, the sound damping canal remaining open during use; and
    an air permeable, sheet-like membrane formed from a second material and supported by the filter housing in a position between the sound inlet opening and the sound outlet opening, the sheet-like membrane extending transverse to the sound damping canal;
  wherein the second material of the sheet-like membrane is manufactured from a sheet of substantially air impermeable material, the second material being flexible with respect to sound waves relative to the first material, the sheet-like member having at least two perforations extending substantially parallel to an axis of the sound damping canal, the perforations rendering the sheet-like membrane air permeable.

2. An ear protector according to claim 1, wherein each perforation has a substantially similar diameter.

3. An ear protector according to claim 1, wherein at least one of the perforations has a diameter substantially equal to a thickness of the sheet-like membrane.

4. An ear protector according to claim 1, wherein the sheet of substantially air impermeable, flexible material is elastic, and wherein the sheet of substantially air impermeable, flexible material is manufactured from a silicone material.

5. An ear protector according to claim 1, wherein at most 5% of a surface of the sheet-like membrane is air-permeable.

6. An ear protector according to claim 1, wherein the sheet-like membrane has a thickness less than about 0.1 mm.

7. An ear protector comprising:
  a housing placeable in an auditory duct of a person, the housing substantially closing the auditory duct to direct sound vibrations, said housing comprising:
    a canal extending from an outer ear housing surface to an inner ear housing surface, the canal remaining open during use; and
    a sound damping filter disposed within the canal, the sound damping filter having a damping canal extending from a sound inlet opening to a sound outlet opening and having an air permeable membrane extending transverse to the damping canal,
  wherein the air permeable membrane is manufactured from a sheet of substantially air impermeable, flexible material having a plurality of perforations extending substantially parallel to an axis of the damping canal, the flexible material being flexible relative to the canal and with respect to sounds.

8. The ear protector of claim 7, wherein the housing and the sound damping filter are formed from different materials.

9. The ear protector of claim 7, wherein the housing is substantially rigid, and wherein the sound damping filter is substantially flexible.

10. The ear protector of claim 7 wherein a damping characteristic of the ear protector is substantially constant for high frequencies.

11. A method for manufacturing an ear protector having a sound damping filter, the method comprising:
  perforating a layer of substantially air impermeable, flexible, and sheet-like material substantially transverse to a planar surface of the sheet-like material to form a membrane having at least one perforation for air transport through the membrane, the sheet-like material being flexible with respect to sounds, wherein the step of perforating comprises:
    scoring the layer of substantially air impermeable, sheet-like material to form the at least one perforation extending a full thickness of the layer; and
    measuring a damping characteristic of the perforated, sheet-like material;
    wherein the steps of scoring and measuring are repeated until a desired low frequency damping characteristic is achieved; and
  fitting the membrane transversely within a canal disposed within a housing, the canal formed from a rigid material relative to the substantially air impermeable, flexible, and sheet-like material, the housing being sized to fit in an auditory canal of a person.

12. A method according to claim 11, wherein subsequent steps of scoring comprise:
  forming perforations of substantially equal diameter.

13. A method according to claim 11, wherein subsequent steps of scoring comprise: increasing the diameter of a previous perforation.

14. A method according to claim 11, wherein a diameter of the at least one perforation is substantially equal to a thickness of the membrane.

15. A method according to claim 11, wherein a diameter of the at least one perforation no greater than 0.1 mm.

16. A method according to claim 12, wherein the step of perforating comprises:
  generating at least one perforation by means of a punching, drilling or laser operation.

17. An ear protector for damping sound, the ear protector comprising:
  a housing sized to fit in an auditory duct of a person, the housing having an ear shell side and an ear drum side, the housing substantially closing off the auditory duct of the person, the housing comprising;
    a canal extending from the ear shell side of the housing to the ear drum side; and
    a sound damping filter positioned within the canal, the sound damping filter comprising:
      a sound damping canal defining a passage extending from a sound inlet opening to a sound outlet opening, the sound damping canal remaining open during use independent of the sound frequency or level of sound pressure; and
      an air permeable, sheet-like membrane positioned between the sound inlet opening and the sound outlet opening, the sheet-like membrane extending transverse to the sound damping canal;
  wherein the sheet-like membrane is manufactured from a sheet of substantially air impermeable, flexible elastic silicone material, the sheet-like membrane having at least one perforation extending substantially parallel to an axis of the sound damping canal, the perforation rendering the sheet-like membrane air permeable.

18. The ear protector of claim 17 wherein a damping characteristic of the ear protector is substantially constant for high frequencies.

19. The ear protector of claim 17 wherein the sheet-like membrane is centered between the sound inlet opening and the sound outlet opening.

20. The ear protector of claim 17 wherein the sheet-like membrane has a thickness of approximately 30 $\mu$m.

21. The ear protector of claim 17 wherein the selected number of perforations is determined according to a desired damping characteristic for frequencies less than 1000 Hz.

22. The ear protector of claim 17 wherein the sound damping filter comprises a tube supporting the sheet-like membrane within the housing, and wherein the housing, the tube and the flexible sheet-like membrane have different relative flexibilities.

23. The ear protector of claim 17 wherein the at least one perforation is a selected number of perforations of approximately equal diameter.

24. The ear protector of claim 17 wherein the sound damping filter comprises a tube supporting the sheet-like membrane within the housing, and wherein the tube comprises:

- a sound inlet wall having a sound inlet opening for receiving sounds and extending transverse to a central axis of the tube;
- a sound outlet wall having a sound outlet opening for allowing sounds to pass and extending transverse to the central axis of the tube; and
- a peripheral wall attached to the sound inlet wall at one end and to the sound outlet wall at another end, the peripheral wall defining a cavity having a greater cross-sectional area than either the sound inlet opening or the sound outlet opening.

* * * * *

UNITED STATES PATENT AND TRADEMARK OFFICE
CERTIFICATE OF CORRECTION

PATENT NO. : 6,691,822 B2
DATED : February 17, 2004
INVENTOR(S) : Victor J.A. Anton Meeussen et al.

It is certified that error appears in the above-identified patent and that said Letters Patent is hereby corrected as shown below:

Title page,
Item [54], Title, insert -- FILTER --, after "SOUND DAMPING"

Signed and Sealed this

Twenty-fifth Day of January, 2005

JON W. DUDAS
*Director of the United States Patent and Trademark Office*

UNITED STATES PATENT AND TRADEMARK OFFICE
CERTIFICATE OF CORRECTION

PATENT NO. : 6,691,822 B2
APPLICATION NO. : 10/200732
DATED : February 17, 2004
INVENTOR(S) : Victor J.A. Anton Meeussen et al.

It is certified that error appears in the above-identified patent and that said Letters Patent is hereby corrected as shown below:

Title Page, (75) Inventors: delete "Victor Joseph Ahton Meussen",
Insert -- Victor Joseph Anton Meussen --

Signed and Sealed this

Twelfth Day of September, 2006

JON W. DUDAS
*Director of the United States Patent and Trademark Office*